United States Patent [19]

Batz

[11] 4,166,380

[45] Sep. 4, 1979

[54] QUANTITATIVE MEASURING SYSTEM FOR COMBUSTIBLE GAS WITH AUDIBLE TICK RATE

[75] Inventor: James E. Batz, Northbrook, Ill.

[73] Assignee: Northern Illinois Gas Company, Aurora, Ill.

[21] Appl. No.: 880,697

[22] Filed: Feb. 23, 1978

[51] Int. Cl.² .................. G08B 17/10; G01N 31/00
[52] U.S. Cl. ................................. 73/23; 340/634
[58] Field of Search .............. 73/23, 27 R; 340/632, 340/633, 634

[56] References Cited

U.S. PATENT DOCUMENTS

| | | | |
|---|---|---|---|
| 2,786,350 | 3/1957 | Johnson | 73/27 R |
| 3,427,862 | 2/1969 | Hubner | 73/23 |
| 3,482,233 | 12/1969 | Ogg | 73/27 R |
| 3,860,919 | 1/1975 | Aker | 340/634 |
| 3,877,291 | 4/1975 | Hoppesch et al. | 73/27 R |
| 3,906,473 | 9/1975 | Le Vine | 340/634 |
| 3,950,739 | 4/1976 | Campman | 340/634 |
| 4,004,452 | 1/1977 | Logothetis et al. | 73/27 R |

Primary Examiner—Stephen A. Kreitman
Attorney, Agent, or Firm—Emrich, Root, O'Keeffe & Lee

[57] ABSTRACT

The instrument uses a semiconductor gas sensor element energized with a regulated voltage source and placed in the atmosphere to be tested to generate a signal representative of the concentration of natural gas in the air. A meter displays the signal to determine whether the area is hazardous, and a variable repetition rate blocking oscillator feeding a speaker is responsive to the signal for generating an audible tick rate useful in locating a leak. The instrument is light-weight, portable, easy to use and intended to comply with industry standards as an intrinsically safe instrument.

7 Claims, 2 Drawing Figures

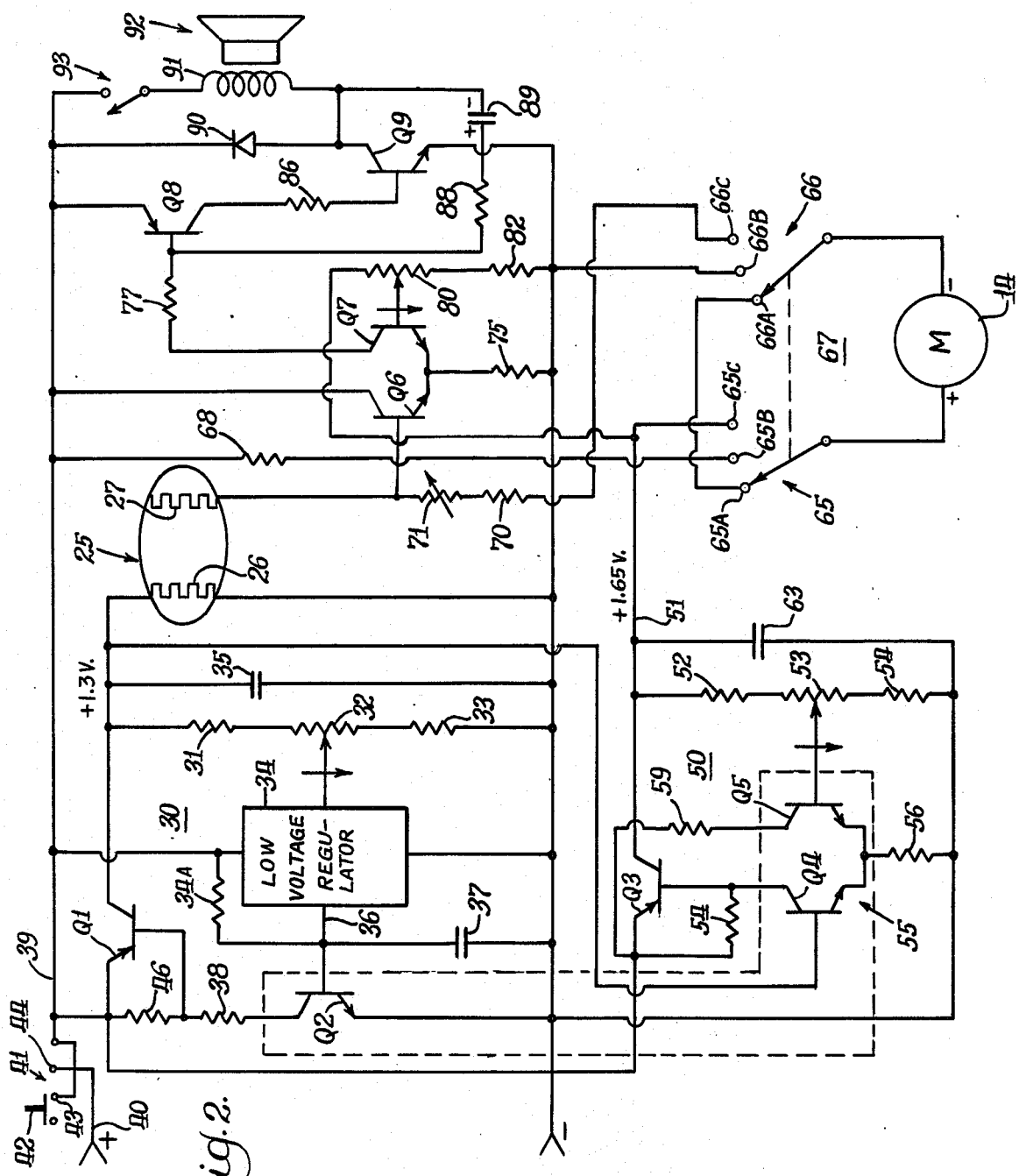
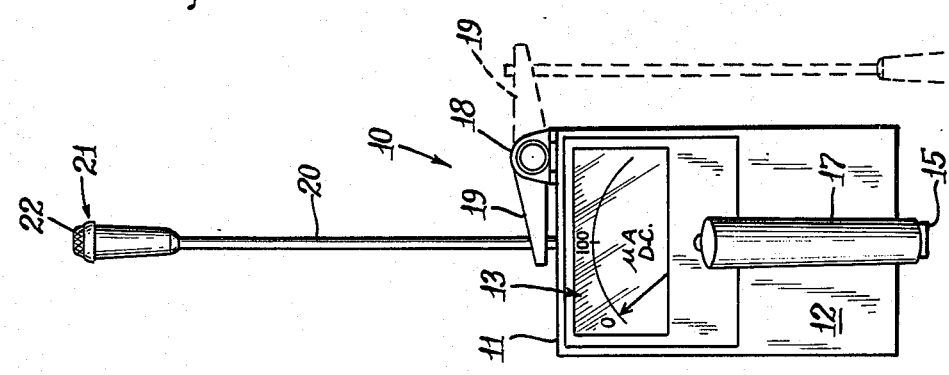

QUANTITATIVE MEASURING SYSTEM FOR COMBUSTIBLE GAS WITH AUDIBLE TICK RATE

BACKGROUND AND SUMMARY

The present invention relates to apparatus for measuring the concentration of a combustible gas; and more particularly, the present invention is designed to give a quantitative measure of the concentration of natural gas in a portable instrument meeting industry standards for "intrinsically safe" devices. Intrinsically safe circuits and apparatus are defined in Underwriters Laboratories, Inc., Publication UL 913, Second Edition, Mar. 20, 1977, *Standard for Intrinsically Safe Electrical Circuits and Apparatus for Use in Hazardous Locations and Its Associated Apparatus*, Part of Section 3.8, as follows: "Intrinsically safe circuits and apparatus—circuits and apparatus incapable of releasing sufficient electrical or thermal energy under normal or abnormal conditions to cause ignition of a specific hazardous atmospheric mixture in its most easily ignited concentration."

The most widely used gas leak detector in the gas industry is a conventional portable instrument which measures the percentage of combustible gas in air and is known in the industry as the Mine Safety Appliance (MSA) Indicator. This unit is portable and battery-powered. The atmosphere to be tested is drawn through the instrument by means of a manually-operated rubber suction bulb. A D'Arsonval-type meter is used to indicate the percentage of combustible gas in the air. In a single-range version, the instrument measures below the lower explosive level of the gaseous mixtures. For natural gas, the lower explosive level (L.E.L.) is approximately 5% natural gas in air. For the range 0 to 5%, a catalytic filament is used to cause combustion of the natural gas. The heat generated from combustion is used to alter the electrical resistance of a filament, the resistance being proportional to temperature which varies in accordance with the percentage of combustible gas in the mixture being measured.

In a dual-range version of this instrument, in addition to the measurement technique just described for measuring the amount of combustible gas in the L.E.L. range, measurement is also possible in the range above 5% of combustible gas; and in this range, a thermal conductivity filament having an electrical resistance which changes in accordance with the amount of combustible gas in the atmosphere being tested is connected in a bridge circuit configuration energized by batteries. On the lower range, these instruments will reliably detect 2,000 to 3,000 ppm.

It is well known in the industry that the explosive range of natural gas in air is approximately 5% to 15% when confined in a closed space. This is a highly dangerous condition, and it is therefore desirable to have a quantitative measure of the concentration of combustible gas. An atmosphere containing more than 15% natural gas also presents a potentially dangerous condition because the concentration must pass through the explosive range when the space is being ventilated. Thus, a calibrated detector giving a quantitative measure of the concentration of a combustible gas is a highly desirable instrument.

In addition to identifying potentially hazardous situations, it is also desirable to use a combustible gas detector to find the source of gas leaks under various situations. For this operation, the instruments described above which reliably detect 2,000 to 3,000 ppm gas in air are not sensitive enough to detect small leaks. In addition, the life of the filament of the instruments described above is short, and the filaments used in the higher range are easily contaminated. Operation of these instruments requires two hands (one to aspirate the mixture being tested and the other to attend to the sample probe), and they are difficult to use in dark areas. Further, because the instrument requires the drawing in of a sample, a large number of samples may have to be taken where there is no hint as to where the leak may be. When used on the L.E.L. range, if the concentration of combustibles in the atmosphere being sampled exceeds 5%, the meter pointer quickly moves to full scale and then reverses to zero. If this is not observed, the operator becomes aware of it after moving past the leak source while continuing to aspirate until fresh air dilutes the gaseous mixture in the filament chamber to the 5% level. The meter pointer again swings to full scale and will slowly move back to zero. The operator must then retrace his steps to find the leak source.

More sensitive instruments are available for detecting gas leaks, and they employ flame ionization techniques. However, these are not considered readily portable instruments, and they are very expensive. These instruments are usually mounted on a truck and used for wide area leak surveys, such as along roads.

In about 1969 a semiconductor gas sensor was developed, as described in U.S. Pat. Nos. 3,631,436; 3,732,519; 3,835,529; and 3,900,815. A combustible gas indicator using these semiconductor devices has been made by T.I.F. Industries, Inc., called a Model CGD 880 which is easy to handle, has an audible signal and is sensitive to natural gas concentrations as low as 200 ppm. However, the instrument is not rated intrinsically safe, and it would not provide reliable quantitative measurements if a meter were added and no other changes made.

The present invention, then, uses a semiconductor gas sensor element which is energized by a highly regulated, stable, very low voltage supply to generate an output signal which is a quantitative measure of natural gas (or other combustible gas if properly calibrated) in air. A meter or other visual indicator displays the signal to determine whether the area is hazardous. A blocking oscillator feeding a speaker is responsive to the measurement signal for generating an audible tick rate useful in locating a leak. Thus, the present invention is useful not only as a measuring instrument, but as a leak detector. Use as a leak detector does not affect the meter reading of gas concentration.

The instrument is lightweight, portable, easy to use; and it is designed to meet industry standards as an intrinsically safe instrument for use in an explosive atmosphere.

The instrument is designed for operation using only a single hand, and it includes a probe at the end of which the gas sensor is mounted. The indicating meter dial is preferably mounted adjacent a handle for the case to facilitate reading since the meter faces the user. The audible signal is adjusted to give a slow ticking sound, and it increases to a faster ticking rate as the concentration of combustible gas increases, as when approaching a gas leak. The audible signal may be switched off in the event it is not desired. A single scale may be used for the entire measurement range—for example, a concentration of about 1% gas in air may read to midscale; from 1% to 5% may read from midscale to above four-fifths of the upper half of the dial; and the remaining one-fifth indicates that the gaseous mixture is above the L.E.L. range. Thus, the instrument is sensitive for locating small gas leaks, and it will indicate when the gaseous mixture is nearing the L.E.L. range, and when it is exceeded.

Other features and advantages of the present invention will be apparent to persons skilled in the art from the following detailed description of a preferred embodiment accompanied by the attached drawing.

THE DRAWING

FIG. 1 is a front view of an instrument incorporating the present invention, showing the probe in the use and the storage position; and FIG. 2 is a circuit schematic diagram of one embodiment of the invention.

DETAILED DESCRIPTION

Referring first to FIG. 1, reference numeral 10 generally designates a lightweight, portable instrument including a casing 11 having a front panel 12 in which there is mounted a meter dial 13 of a conventional DC microammeter, designated 14 in FIG. 2.

To the bottom of the casing 11 there is mounted a forwardly extending bracket 15 which is provided at its distal end with an upwardly and outwardly extending handle 17.

To the top of the casing 11 a mounting bracket 18 is affixed. An extension 19 is pivotally mounted to the bracket 18 for movement between a use position (shown in solid line) and a storage or transportation position (shown in dash line).

A tubular probe 20 is mounted to the extension 19; and at the end of the probe 20, a semiconductor gas detector assembly generally designated 21 is secured. A screen 22 is included in the gas detector assembly 21 to permit the gas and air mixture to flow over the semiconductor sensing element while protecting the semiconductor sensing element.

As seen in FIG. 1, when the handle 17 is held in one hand, the meter dial 13 may easily be seen, and the probe 20 is in a position for placement for leak detection with the leak detector assembly 21 located at some distance from the meter so as to facilitate its placement and use in remote locations.

Referring now to FIG. 2, the semiconductor gas detector is generally designated 25, and it includes first and second heater elements 26, 27. The sensor 25 may be a gas-electric transducer of the type marketed by Figaro Engineering Inc. of Osaka, Japan. It is a sintered n-type semiconductor bulk device composed mainly of tin dioxide wherein the conductivity of the device between the two heaters 26, 27 increases with increasing concentration of a combustible gas such as hydrogen, carbon monoxide, methane, ethane, propane or natural gas, or organic solvent vapors.

In order to insure that the instrument qualify as an intrinsically safe device, very low voltages are used. Hence, one terminal of the heater element 26 is connected to a regulated voltage of +1.3 v., and the other terminal of that heater element is connected to common (which is the negative of the battery supply). The +1.3 v. is provided from a voltage regulator generally designated by reference numeral 30. A voltage divider network including a fixed resistor 31, a variable resistor 32 and a fixed resistor 33 are connected in series between the +1.3 v. line and common. A capacitor 35 provides a low AC impedance to the output of the 1.3 v. regulator.

The voltage on the wiper arm of the potentiometer 32 is fed to an input of a low voltage regulator 34. The low voltage regulator 34 may be a circuit such as that marketed by Intersil, Inc. of Cupertino, California under the designation ICL8212. The circuit is a low-voltage regulator including a reference source and an error amplifier. It takes its reference from the wiper arm of the potentiometer 32 and generates an output voltage on the line 36. A resistor 34A provides a load for the output stage of the low voltage regulator 34. A capacitor 37 compensates for any phase shifts between the input and output of the low voltage regulator. The line 36 is connected to the base of a transistor Q2, the collector of which is connected to a resistor 38 to the base of a transistor Q1. The emitter of transistor Q1 is connected to a line 39 which is normally connected to the positive terminal 40 of the battery during operation. A two-position slider switch generally designated by reference numeral 41 is interposed between the battery terminal 40 and a line 39 to turn power on and off. In the "OFF" position shown, the battery terminal 40 is disconnected from the line 39. In the "ON" position terminals 43 and 44 are shorted, causing the positive supply to be coupled to the line 39.

Returning now to the voltage regulator 30, when the switch 42 is turned on, a current is fed through transistor Q1, and the collector voltage of transistor Q1 is maintained at +1.3 volts with respect to the minus supply terminal by the low voltage regulator 34 and the transistor Q2. Establishing a reference voltage from the potentiometer 32, the low voltage regulator 34 cooperates with transistor Q2 to vary the base drive current of transistor Q1 in such a manner as to maintain the collector-to-common voltage constant despite changes in the battery terminal voltage and sensor heater current with time. Thus, the source energizing the heater element 26 is a highly regulated, low voltage source; and this is considered to be an important element (together with the high degree of regulation of the 1.65 volt source to be discussed) in achieving a principal object of the invention--namely, the ability to obtain a reliable quantitative measurement of the concentration of combustible gas.

Referring now to the lower left hand portion of FIG. 2, a second voltage regulator is generally designated 50, and it generates an output voltage of +1.65 v. on line 51.

The voltage regulator 50 includes a fixed resistor 52, a potentiometer 53, and a fixed resistor 54 connected in series between the line 51 and common. The wiper arm of the potentiometer 53 is connected to one input of a differential error amplifier generally designated 55 and comprising, as active elements, transistors Q4 and Q5 having their emitters connected in common to a resistor 56. The base of transistor Q4 is connected to the 1.3 v. supply line (serving as a reference). The collector of transistor Q4 is connected to the base of a transistor Q3. A resistor 54 is connected from the collector of Q4 to line 39, providing a collector load for Q4. The emitter of transistor Q3 is connected to the positive supply. The collector of transistor Q3 is directly connected to the line 51.

The voltage on the line 51 is operated as follows: If the voltage reduces, then the input voltage to transistor Q5 taken from the potentiometer 53 is also reduced.

This causes less current to flow through transistor Q5, thereby reducing the voltage drop across resistor 56. This causes transistor Q4 to conduct more; and this, in turn, draws additional base current through transistor Q3. This will increase the collector current of transistor Q3, thereby increasing the voltage on line 51. To summarize, the transistors Q4 and Q5 act as a differential amplifier (the base of transistor Q4 being connected to the +1.3 volt reference and the base of transistor Q5 acting as the signal input). The differential output current signal drives the base of the "pass" transistor Q3. Capacitor 63 presents a low AC load impedance to the regulator.

The terminals of the meter 14 are connected respectively to first and second decks 65, 66 of a three-position switch generally designated 67. The wiper arms of the decks 65, 66 are mechanically ganged, as illustrated. In the position illustrated, the meter 14 is disconnected from the rest of the circuitry, the positions 65A and 66A being shorted. The terminal 65B is connected through a resistor 68 to the line 39. The position 65C is connected to the highly regulated +1.65 v. source. The terminal 66B is connected to common. The terminal 66C is connected through a fixed resistor 70 and a varible resistor 71 to the element 27 of the semiconductor sensor 25 (which, in the illustrated embodiment, acts as an electrode or collector).

The third position (C) of the switch 67 is used for measurement purposes. In this position, there is a series circuit between the highly regulated +1.65 v. source on line 51 and common; and it comprises the meter 14, the fixed resistor 70, the variable calibration resistor 71, and the variable resistance gas-electric transducer 25. As the concentration of combustible gas increases in the environment being measured, the resistance between the elements 26 and 27 decreases, thereby causing more current to flow through the meter 14 and giving an increasing reading. Thus, the use of this second highly regulated, low voltage source in the measuring circuit also cooperates in achieving a reliable quantitative measurement in an intrinsically safe device.

It will also be observed that the signal taken at the junction between variable resistor 71 and heater element 27 is related to the concentration of combustible gas detected. That is, this voltage (referenced to common or negative) decreases as the concentration of gas increases. This signal is fed to the base of a transistor Q6, the emitter of which is connected in common with the emitter of a transistor Q7. This common junction is connected through a resistor 75 to common. The collector of transistor Q6 is connected to the positive supply line 39, and the collector of transistor Q7 is connected through a resistor 77 to the base terminal of a transistor Q8.

The transistors Q6 and Q7 form a differential error amplifier similar to the one previously described. The reference voltage is derived from a potentiometer 80 connected between the line 51 and a fixed resistor 82 connected to ground. The wiper arm is connected to the base of the transistor Q7 and generates a reference voltage. As the input signal at the base of transistor Q6 decreases (in response to an increase in sensed combustible gas concentration), the current through transistor Q6 decreases, thereby causing transistor Q7 to conduct more current. Transistor Q8 is connected with a transistor Q9 so as to form a blocking oscillator. A resistor 88 and capacitor 89 are connected between the collector of transistor Q9 and the base of transistor Q8. The collector of transistor Q8 is connected to the base of transistor Q9 via resistor 86 which limits the base drive current for transistor Q9. The collector of transistor Q9 is connected to the anode of a diode 90, the cathode of which is connected to the positive line 39. Similarly, the collector of transistor Q9 is connected to the coil 91 of a speaker 92. The other side of the coil is connected to the positive line 39 through a switch 93.

The variable frequency blocking oscillator operates as follows. When transistor Q8 conducts, transistor Q9 also conducts. Both transistors are saturated in a very short time. When transistor Q9 conducts, the coil 91 is connected across the battery terminals; and the capacitor 89 charges through resistor 88 in the polarity indicated. When the charge on the capacitor reaches a level sufficient to cause transistor Q8 to conduct less, transistor Q9 also conducts less current. Positive feedback then causes both transistors to shut off; and the charge on capacitor 89 begins to dissipate through the resistor 77, transistor Q7 and resistor 75. This continues until the voltage at the base of transistor Q8 has reduced to a point where transistor Q8 will conduct again.

When an increasing concentration of combustible gas is detected, as mentioned above, the resistance of the sensor 25 decreases, thereby causing transistor Q6 of the differential error amplifier to conduct less current, and causing transistor Q7 to conduct more current. The additional current conducted by transistor Q7 will cause the capacitor 89 to discharge more quickly, thereby increasing the repetition rate of the blocking oscillator, and the audible signal generated by the speaker 92.

To calibrate the instrument, the first step is to check the +1.3 v. heater supply and the +1.65 v. supply. The switch 41 is set to the ON position in which the terminals 43, 44 are shorted. The switch 67 is set to the first (OFF) position. This position is also used to damp the meter movement for transportation. A wait of one-two minutes is required to permit the heater 26 to stabilize. After two minutes, the switch 67 is switched to the second position (BATTERY TEST), thereby permitting current to flow through resistor 68 and the meter 14 to determine the condition of the batteries. The resistor 68 is chosen so that the current meter 14 will display a certain level if the battery voltage is above a predetermined level. A battery supply voltage of 2.0 v. or higher is registered as acceptable or "GOOD". If this reading is not obtained, the batteries must be replaced or recharged.

Next, the +1.3 v. is adjusted by means of the potentiometer 32 to within 2 millivolts of the nominal 1.3 v., using a digital voltmeter or other accurate voltmeter. Next, by adjusting potentiometer 53, the voltage at line 51 is set to be within 2 millivolts of the nominal 1.65 v. as previously described.

Before adjusting for the L.E.L. setting, the sensor 25 should be conditioned, especially when the device has not been used for several days. When switch 41 is placed in the ON position and function switch 67 is in position 3 (GAS CONCENTRATION), meter 14 will rise to full scale and slowly reduce to the background region of the scale. This should occur in approximately one minute if the sensor is properly conditioned. Conditioning is accomplished, should this not occur, by turning switch 41 to the ON position for two minutes and then to OFF for ten minutes until the meter 14 exhibits the proper response explained above. This may take five to ten cycles of preheating the heater element 26.

Calibration is accomplished by placing the sensor 25 in a test L.E.L. atmosphere of known concentration and adjusting resistor 71 to obtain a reading on meter 14 equal to that of the known concentration of the test atmosphere.

The instrument which has been disclosed is designed for using two 1.5 v. "D" size cells in series.

After the instrument is calibrated as described above, operation proceeds as has already been disclosed. Concentrations of less than 250 ppm. can be detected using either the meter 14 or the audible ticking rate from the speaker 92. Equivalent visual indicator means, such as light emitting diodes, may be used in combination with a scale, for example, in place of the meter 14 where it is desired to increase its ability to withstand abuse or to reduce cost.

As previously indicated, approximately one-half of the meter scale is used for quantitative measurement of combustible gas concentration from the low range (approximately 250 ppm.) up to about 1%. Four-fifths of the upper half of the dial displays a reading of 1% to 5% concentration of combustible gas; and the remaining one-fifth of the upper half of the dial indicates that the gaseous mixture is above the L.E.L. range.

In summary, the present instrument gives a reliable quantitative measure of detected combustible gas through the L.E.L. range, and an audible ticking rate, the repetition rate of which is representative of the concentration of combustible gas detected.

Having thus described in detail one embodiment of the invention, persons skilled in the art will be able to modify certain of the structure which has been illustrated and to substitute equivalent elements for those disclosed while continuing to practice the principle of the invention; and it is, therefore, intended, that all such modifications and substitutions be convered as they are embraced within the spirit and scope of the appended claims.

I claim:

1. Apparatus for measuring combustible gas comprising: semiconductor sensor means including a heater element and a collector electrode, the resistance between said element and said electrode decreasing with an increasing concentration of combustible gas in an atmosphere in which said sensor means is placed for generating an output signal representative of said concentration; a source of electrical energy; a meter; calibration circuit means for calibrating the output signal of said sensor means; means for connecting said meter in circuit with said collector electrode of said sensor means and said calibration means for measuring the current through said sensor means, said current being a reliable quantitative measure of the concentration of combustible gas detected by said sensor means; regulated, low voltage circuit means connected to said source for supplying a highly regulated, low voltage to said heater element of said sensor means and to the circuit comprising said meter, said calibration circuit means and said collector electrode of said sensor means; and audible circuit means including a variable repetition rate blocking oscillator and a loudspeaker connected to the output of said oscillator responsive to the output signal of said sensor means for generating an audible ticking signal having a repetition rate representative of the concentration of said gas.

2. The apparatus of claim 1 further comprising a manually operated switch connected in circuit with said speaker for disabling said speaker.

3. The apparatus of claim 1 wherein said source comprises battery means and said system further comprises function switch means connected in circuit with said meter; said calibration circuit means including resistor means connected to said battery means, said function switch means being adapted to connect said meter in circuit with said calibration resistor means to test the condition of said battery means in one position of said function switch means.

4. The apparatus of claim 1 wherein said source comprises batteries and wherein said apparatus includes a housing for mounting said circuitry and said meter; a probe; and means for mounting said sensor means at the distal end of said probe.

5. The apparatus of claim 4 further comprising a handle mounted to said casing and extending beneath and in front of said meter whereby when said handle is held in one hand, a person holding said instrument can read said meter directly.

6. The apparatus of claim 5 further comprising mounting means for mounting said probe to the outside of said casing for permitting said probe to be secured in a first position extending perpendicular to a surface of said casing for use, and a second position in which said probe extends parallel to a surface of said casing for storage or transportation.

7. Apparatus for measuring combustible gas comprising: semiconductor sensor means including a heater element and a collector electrode, the resistance between said element and said electrode decreasing with an increasing concentration of combustible gas in an atmosphere in which said sensor means is placed for generating an output signal representative of said concentration; a source of electrical energy; measuring means; calibration circuit means for calibrating the output signal of said sensor means; means for connecting said measuring means in circuit with said collector electrode of said sensor means and said calibration means for measuring the current through said sensor means, said current being a reliable quantitative measure of the concentration of combustible gas detected by said sensor means; regulated, low voltage circuit means connected to said source for supplying a highly regulated, low voltage to said heater element of said sensor means and to the circuit comprising said measuring means, said calibration circuit means and said collector electrode of said sensor means; and audible circuit means including a variable repetition rate blocking oscillator and a loudspeaker connected to the output of said oscillator responsive to the output signal of said sensor means for generating an audible ticking signal having a repetition rate representative of the concentration of said gas.

* * * * *